(12) United States Patent
Komatsu et al.

(10) Patent No.: US 9,086,404 B2
(45) Date of Patent: Jul. 21, 2015

(54) METHOD FOR TREATING LIVING SAMPLES AND ANALYZING THE SAME

(75) Inventors: Manabu Komatsu, Kawasaki (JP); Hiroyuki Hashimoto, Yokohama (JP); Kazuhiro Ban, Tokyo (JP); Yohei Murayama, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1887 days.

(21) Appl. No.: 11/867,276

(22) Filed: Oct. 4, 2007

(65) Prior Publication Data

US 2008/0090267 A1 Apr. 17, 2008

(30) Foreign Application Priority Data

Oct. 11, 2006 (JP) ................... 2006-277385

(51) Int. Cl.
*G01N 33/50* (2006.01)
*G01N 35/10* (2006.01)

(52) U.S. Cl.
CPC ........ *G01N 33/5082* (2013.01); *G01N 35/1002* (2013.01); *G01N 2035/1041* (2013.01)

(58) Field of Classification Search
CPC ............ C12Q 1/02; C12Q 1/025; C12Q 1/04; C12Q 1/00; C12N 11/00; C12M 1/34; C12M 1/343; C12M 3/00
See application file for complete search history.

(56) References Cited

U.S. PATENT DOCUMENTS

| | | | |
|---|---|---|---|
| 6,057,165 A * | 5/2000 | Mansour | ........ 436/518 |
| 7,188,031 B1 | 3/2007 | Okamoto et al. | |
| 2004/0067482 A1 * | 4/2004 | Yasuda et al. | ........ 435/4 |
| 2004/0132080 A1 | 7/2004 | Kawaguchi et al. | |
| 2004/0137420 A1 | 7/2004 | Yasuda et al. | |
| 2004/0219588 A1 | 11/2004 | Furuta | |
| 2007/0105087 A1 | 5/2007 | Ban et al. | |
| 2008/0108132 A1 | 5/2008 | Ban et al. | |
| 2008/0268497 A1 | 10/2008 | Hashimoto et al. | |
| 2009/0130776 A1 | 5/2009 | Imamura et al. | |
| 2009/0148346 A1 | 6/2009 | Ban et al. | |

FOREIGN PATENT DOCUMENTS

| | | |
|---|---|---|
| JP | 2001-249125 A | 9/2001 |
| JP | 2004-85546 A | 3/2004 |
| JP | 2006-105653 A | 4/2004 |
| JP | 2004-347594 A | 12/2004 |
| JP | 2005-61996 A | 3/2005 |
| WO | 2005/003715 A2 | 1/2005 |

\* cited by examiner

*Primary Examiner* — Taeyoon Kim
*Assistant Examiner* — Srikanth Patury
(74) *Attorney, Agent, or Firm* — Fitzpatrick, Cella, Harper and Scinto

(57) ABSTRACT

A method is provided by which a reagent is provided to a living sample, including contacting a thin-film containing a porous body with a living sample containing cells or tissues, and discharging a solution containing at least one or more reagents to a non-contact side of the thin-film by ink-jet to provide the solution to the specific area of the living sample through pores on the thin-film, wherein the smaller diameter of the pores on the porous body relative to the diameter of cells in the living sample enables the reagent to be provided to each individual cell separately. According to this method, the reagent and the reaction product can be fixed while maintaining positioning information of the target substance in the living sample, as a pretreatment for analyzing with high positioning accuracy the target substance in each individual cell in the living sample.

5 Claims, 3 Drawing Sheets

METHOD FOR TREATING LIVING SAMPLES AND ANALYZING THE SAME

BACKGROUND OF THE INVENTION

1. Field of the Invention

The present invention belongs to a medical and biology field such as cell biology, pathology and biochemistry, and in particular relates to a method for reacting a reagent to a living sample and a method for detecting a reaction product.

2. Description of the Related Art

Due to the recent development of genome analysis, the importance of analysis of protein which is a gene product present in a living body has rapidly attracted considerable attention. Among others, the importance of protein analysis in tissue sections is being recognized. For example, many attempts have been made to elucidate the proteins in cancer tissue sections which are involved in recurrence and metastasis. Microscopic observation has often been used as a method for analyzing surface proteins in living samples of cells and tissues. In this case, methods have been used in which a target substance is labeled through a specific antibody, and the color, light emission, fluorescence or the like of the label is detected to identify the protein target. Recently, for example a method is described in Japanese Patent Application Laid-Open No. 2001-249125 in which a sample section is directly irradiated with a laser to obtain a mass spectrum. Further, for means of directly treating the surface of a living sample, analysis of the living sample has been performed by directly applying a reagent to the living sample whose amount and position has been controlled using an ink-jet method as described in Japanese Patent Application Laid-Open No. 2004-347594. Still further, for visualizing two dimensional distribution of protein and the like in fine details at cellular level in a living sample, a method and a device to obtain information based on the TOF-SIMS method (the time-of-flight secondary ion mass spectrometry) are disclosed in the International Publication No. WO2005/003715. In this method, after directly applying ionizing agents and/or digestive enzymes to the living sample using an ink-jet method or the like, while keeping the positional information, the TOF-SIMS method that has a high space resolving power in sub-micrometer level is performed. By this method, the information related to the kind of proteins in the reaction product (including the information as to the limited digested peptides by the digestive enzyme) can be visualized.

Information as to the distribution of a reaction product in a living sample can be obtained by the methods described in the Japanese Patent Application Laid-Open No. 2004-347594 and International Publication No. WO2005/003715. However, to obtain the two dimensional distribution information in a finer level such as the distribution within a cell size diameter (10 μm), an improvement for the method of discharging droplets in the ink-jet is required. This is because, although the volume of the droplet of the ink-jet for supplying reagents is normally as small as 1 pl-100 pl, the dot size diameter, when dropped on the living sample, becomes as large as 10 μm to 1000 μm. For this reason, when the objective is to obtain the information within a normal single cell size range, problems arise such as widening of the distribution due to the diffusion and elution of the reagents, or lowering of the reaction conditions due to the evaporation of the reagents. Therefore, when the information of the two dimensional distribution within the single cell size range is to be obtained, the reagent must be applied individually in a finer region of the living sample, and held there for a certain period of time until the reaction is completed while preventing the diffusion and evaporation of the droplet as much as possible. If the two dimensional distribution of the sample and the reaction products can be analyzed more accurately for proteins in cells in a specific lesion such as cancer cells or proteins in the neighboring cells to the cancer cells in a living sample analysis, it would contribute to the development of a diagnostic device and drug discovery device.

SUMMARY OF THE INVENTION

Thus, the objective of the present invention is to analyze specific structures or the component molecules in each individual cell in the living sample with high accuracy positioning, and as the preliminary treatment for the analysis, it is the task of the present invention, to provide a method for treating the living sample to fix reagents and reaction products while maintaining at the cellular level the specific structure in the living sample and the information of the positioning of the component molecules, and a method for the analysis.

The present inventors have investigated with much effort to find that the aforementioned objective can be achieved using ink-jet technology and a thin-film containing a porous body in combination to complete the present invention. When the term "ink-jet" is used in the present invention, the solution used herein is not limited to colored liquid (so-called ink) but may be a colorless solution. In that sense, the ink-jet method in the present invention can be referred to as the liquid discharging method.

A first method of the present invention is a method for providing a reagent to a living sample, including contacting a thin-film containing a porous body with a living sample containing cells or a tissue and discharging a solution containing at least one or more reagents to the non-contact side of the film by ink-jet to provide the solution to the specific area of the living sample through pores on the thin-film, wherein the smaller diameter of the pores on the porous body relative to the diameter of cells in the living sample enables the reagent to be provided to each individual cell separately. Here, "diameter of cells" refers to the minor axis of the cells included in the living sample.

A second method of the present invention is a method for treating a living sample with a reagent including providing a reagent solution to a specific area of the living sample according to the first method and further including performing a reactive production while keeping the reagent solution to the specific area, wherein the reagent treatment can be performed by discriminating each individual cell.

A third method of the present invention is a method for analyzing a living sample including treating a specific area of a living sample according to the second method of the present invention and analyzing the specific area treated with a reagent by a microscopic observation or mass spectrometry, wherein positioning information of a target substance can be analyzed in each cell.

The present invention is directed to a method for providing a reagent to a living sample comprising the steps of: contacting a thin-film comprised of a porous body with a living sample containing a cell or tissue, and discharging a solution containing at least one kind of reagent to a non-contact side of the thin-film by ink-jet to provide the solution to a specific area of the living sample through pores of the thin-film, wherein the pore has a diameter smaller than those of the cells or tissues, which enables the reagent to be provided to each of the cells or tissues, distinguishing the cells or tissues.

The thin-film can be almost perpendicularly perforated by the pores.

The diameter of the pore can be in the range of from 10 nm to 10 µm.

In the method for providing a reagent to a living sample, at least one kind of the reagents can be a compound that reacts chemically or biologically with a target substance in the cell or tissue and/or a substance that binds peculiarly to the cell or tissue. The substance can be a living substance comprised of a polypeptide and/or a compound having a binding property the same as or similar to that of the living substance.

The method for providing a reagent to a living sample can further comprises the steps of reading an image information of the living sample and recording a positioning information to provide the reagent to the specific area of the living sample by ink-jet in accordance with the image information.

The present invention is directed to a method for treating a living sample with a reagent, comprising the steps of: providing a solution of reagent to a specific area of a living sample by the above method for providing a reagent to a living sample, and holding the solution of reagent in the specific area to carry out a reactive production, which enables the cells or tissues to be treated with the reagent, distinguishing the cells or tissues.

The present invention is directed to a method for analyzing a living sample, comprising the steps of: treating a specific area of a living sample by the above method for treating the living sample with a reagent, and analyzing the specific area treated with the reagent by a microscopic observation or a mass spectrometry, which enables a positioning information of a target substance by each of the cells or tissues.

Further features of the present invention will become apparent from the following description of exemplary embodiments with reference to the attached drawings.

BRIEF DESCRIPTION OF THE DRAWINGS

FIG. 2A illustrates a continuous mesh structure by mesh 21. FIG. 2B illustrates a pore structure containing independent pores 22. FIG. 2C illustrates a pore structure containing almost perpendicular pores 23. FIG. 2D illustrates a porous body containing aggregated bodies of fine particles 24. FIG. 2E illustrates a porous body having spherical pores 25.

FIG. 3A is a view illustrating the situation where the porous body comes into contact with a living sample, and an enzyme is dispensed to the pores of the porous body. FIG. 3B is an SIMS image profile of protein in the living sample.

DESCRIPTION OF THE EMBODIMENTS

In the present invention, distribution across a thin-film containing a porous body is performed by providing a reagent solution to a specific area of a living sample by an ink-jet method. By providing the reagent solution to the specific area of the living sample through the porous body, the reagent is dispensed and held to a specific structure and component molecules in cells and tissues in the living sample while maintaining their positioning information. The component molecule of the specific structure can be a target substance. The distribution of a reagent by providing droplets is herein referred to as dispension. To maintain the positioning information means that the positioning information of a specific structure or the component molecule thereof after the dispension of the reagent or succeeding reactive production is substantially the same as that before the dispension or when living. The positioning information can be maintained at least within the range of the cell or tissue containing the specific structure or the target substance and can be further maintained within the range of the specific structure in the cell containing the target substance. When analyzing the specific structure or component molecules thereof in the cell or tissue, a molecule composing the specific structure, preferably a characteristic molecule for the specific structure, more preferably a molecule specifically present in the specific structure can be used suitably for the target substance.

A specific structure may be, for example, a structure formed specifically in cancer tissue or cancer cells, and includes a component molecule of these structures, for example, protein and lipid, and preferably a component molecule that is specific to the specific structure, such as cancer specific antigens. Needless to say, pathological tissues or cells of not only cancer but also all diseases and sicknesses may be the subject of the present invention.

Figure 1A:
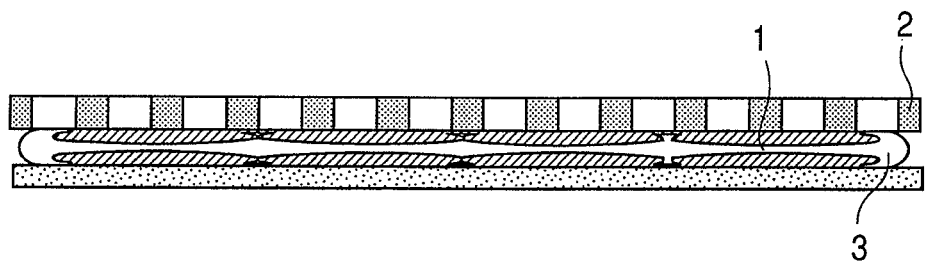
FIGS. 1A, 1B and 1C illustrate schematic views of the living sample treatments of the present invention.
Figure 1B:
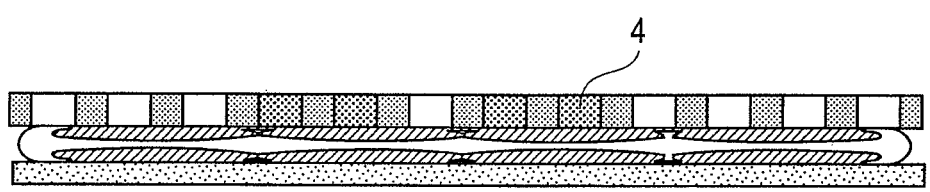
Figure 1C:
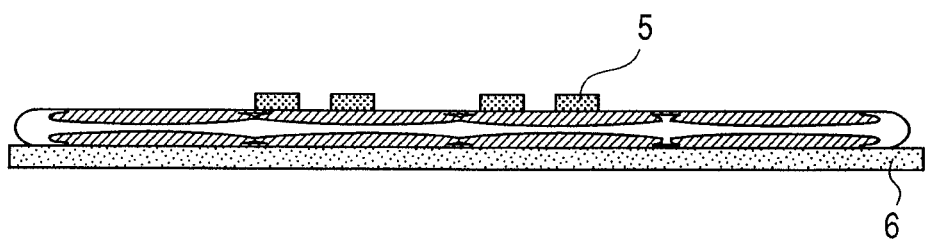

Still further, in the present invention an analysis can be performed after treating a living sample with a reagent by performing a reactive production by distributing the reagent through the porous body using the ink-jet method (FIGS. 1A to 1C), preferably after making the target substance recognizable by a reagent that can make the target molecule recognizable. In the figures, numeral 1 denotes a cell; numeral 2 denotes a porous body; numeral 3 denotes living tissue; numeral 4 denotes a region in which the reagent has been distributed; numeral 5 denotes a reaction product; and numeral 6 denotes a supporting member. The analysis can be performed using methods such as microscopic observation and mass spectrometry.

The living sample in the present invention includes cells and tissues of organisms that are not fixed solid. Cells and tissues can be used in the conditions in which the fine structures in the living body are maintained. To obtain such conditions, cells and tissues that are embedded into an appropriate embedding agent may be used. Since the living samples that maintain the fine structures in a living body can be used, the localization of the target substance to be analyzed by the present invention can be morphologically investigated as the same as in the living body. The living sample described above can be used by attaching to a support made of, for example, glass, resin and metal, or by transferring electronically to a membrane. These samples may be optionally pretreated by staining, washing desalting and the like by the standard methods.

The thin-film containing the porous body of the present invention is used by contacting with a living sample and the pore of the porous body described above is provided with at least one or more of the reagents. The function of the porous body of the present invention is to contact the reagent in the pore with the living body with a good positioning accuracy and to promote a sufficient reactive production by maintaining the droplet for a certain period of time.

When used for the living sample, the reagent is used as liquid. Therefore, the material used for the porous body may be water resistant and not inhibitory to the reactivity of the reagent, and the surface of the porous body may be coated with such a material. Examples of such a material include an organic material, inorganic material, metal, metal oxide film and ceramic, but not limited to these. Further, the surface of the pore of the porous body (inner wall of the pore) is preferably hydrophilic. By making the surface of the pore hydrophilic, liquid can be introduced and held more easily and an enzyme as an aqueous solution can be used conveniently.

Further, the pore diameter of the porous body is preferably smaller than the diameter of cells included in the living samples. Therefore, the pore diameter of the porous body is preferably from 10 nm to 10 µm. When the pore diameter is smaller than 10 nm, problems may occur that the reagent solution is difficult to be held inside of the pore and to be transported across the pore. In the case where the pore diameter is over 10 µm, the pore size becomes equal to or greater than the cell size, and it is more likely that the reagent reaction occurs over a plurality of cells. As a result, there is a possibility that the accuracy would be lower when an analysis is performed while holding the positioning information in each cell. When the pore diameter is not uniform in the direction of the depth, it would be desirable that the pore diameter on the contact surface with the living sample is 10 µm or less. Examples of such cases include a pore shaped like a half corn (the tip side of the corn is the contact surface) and a ball shaped pore (see FIG. 2E). More preferable pore diameter is between 1 µm and 10 µm when the injection of the reagent solution is considered. If the cross section of the pore is not a perfect circle, the pore diameter is defined as the shortest cross section axis of the pore (the shortest width).

Figure 2A:
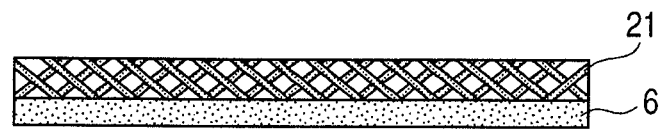
FIGS. 2A, 2B, 2C, 2D and 2E illustrate descriptive views of the thin-film of the present invention containing the porous body.
Figure 2B:
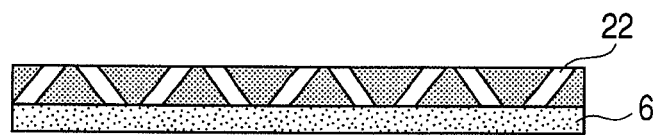
Figure 2C:
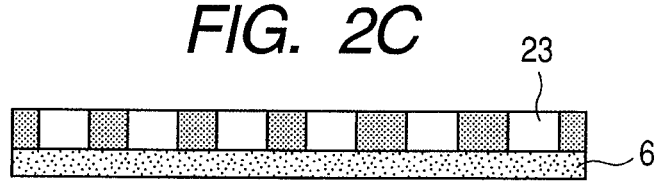

The pore structure of the porous body is not particularly restricted as long as the structure allows dispension of the reagent solution to the living sample with positioning accuracy. That is, any structure can be used as long as the pore perforates from a top face of the porous body (the top face in the present invention is the opposite face that contacts with the living sample) to the face that contacts the living sample. For example, even with a continuous net structure like the one shown in FIG. 2A, the reagent solution can be dispensed and reacted before spreading too far on the two dimensional plane in the porous body if the structure is sufficiently dense or the porous body is sufficiently thin shape. Furthermore, the pores can be structured so that individual pore is independently present. As shown in FIG. 2B, when each pore is not interconnected to each other and present independently, the accuracy of the positioning information can be increased by preventing the diffusion in the direction of the two dimensional plane. Still further, as shown in FIG. 2C, the pore is desirably almost vertical to the contact plane of the living sample. As used herein "almost vertical" includes the concept of "vertical" and the angle of 15° or less from the vertical axis. If the pores have a vertical structure, the reagent solution is delivered quickly and the accuracy of the positioning information can be further improved.

The thickness of the thin-film containing the porous body is not particularly restricted as long as the reagent solution can be dispensed accurately and is preferably in the range between 1 µm and 10 µm. It needs to be noted that if the film is too thin, a part of the thin-film remaining on the surface of the living sample is likely to occur when removing the film from the living sample, and if it is too thick, the positioning accuracy decreases due to aberration of the direction of the perforation.

The size of the thin-film containing the porous body is not particularly restricted as long as the area to be analyzed on the living sample can be efficiently contacted thereby as described above. By considering work efficiency of contact and removal of the thin-film, the thin-film can be prepared to be larger than the living sample by about 5 mm.

Figure 2D:
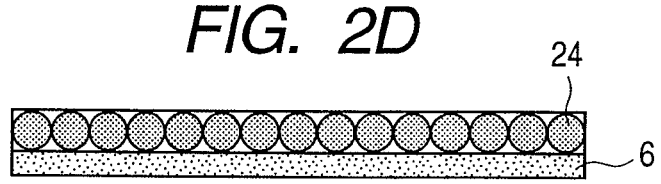
Figure 2E:
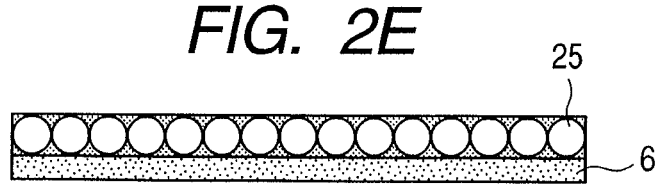

The thin-film containing the porous body as described above can be formed by a general patterning technology. For example, so-called semiconductor processing technologies such as photolithography, electron beam lithography and X-ray lithography, and laser processing technology, machine processing technology and the like can be used. Furthermore, technologies other than these top-down methods can be used. Various technologies, for example, technologies for forming a fine pattern using phase separation of polymers and inorganic substances, for forming pores by anode oxidation of a metal or forming pores by using templates such as water droplets and surfactant micelles, can be used. Also, as shown in FIG. 2D, using an aggregate of fine particles as a porous body, the space between the particles can be used as pores. Conversely, as shown in FIG. 2E, a porous body having spherical pores can be used.

The reagent solution is dispensed to a specific area of the living sample prepared as described above. In the present invention, an ink-jet method is used as a method for dispension to provide and attach droplets of the reagent solution to the specific area. The mechanism of the ink-jet method used in the present invention includes, for example, a piezo-jet method using a mechanical pressure pulse method (piezo) and a film boiling method by an electric heat converter (bubble jet (registered trade name)), but not restricted to these.

In the dispension method of the present invention, an extremely small amount of the reagent can be discharged using the ink-jet method. At this time, the amount of the reagent discharged once from an ink-jet discharge unit (amount of one liquid droplet) can be controlled to be, for example, a few pl, but the amount can be controlled to be much smaller depending on the mechanism of the ink-jet. Also, since the discharge can be repeated, the reagent can be supplied continuously, and for this reason, the upper limit of the amount to be dispensed is not particularly limited. To a specific area, for example, a nano liter level, normally about 100 nl of a reagent can be dispensed. An embodiment, by which the ink-jet discharge unit having a plurality of discharge outlets provides reagents to a specific area by discharging a plurality of droplets at the same time, is also included in the present invention. By discharging a plurality of liquid droplets to a spot, the treatment can be performed while controlling the kind, concentration and amount of discharge of the reagents.

Supplying the reagent continuously with appropriate time intervals, a suitable reaction conditions can be maintained by preventing a loss of the reagent by evaporation. Also, since only the minimum necessary amount of reagent is consumed, big cost cutting can be achieved even if a rare and expensive reagent such as an antigen solution is used.

In the present invention, for example, a discharge of about 1 pl produces a very small dispension range of a diameter of about 10 µm. Using this very small dispension range, the reagent can be dispensed to a pore located in the range of a specific cell by discriminating each one of cell (by discriminating each individual cell). In another words, the dispension to each cell can be achieved. By a certain ink-jet mechanism, the range of distribution can be limited further to a smaller area. To treat each cell with the reagent separately, it is desirable that the reagent is not mixed between the pores, and to achieve this, the amount of injection should be controlled so that the reagent to be dispensed is separated between the pores.

Also, two or more specific areas can be established in the same living sample. Thus, different kinds of the reagents can be added to the different areas of the same living sample, and a plurality of analyses can be performed.

Further, the image information of the living sample can be read before the addition of the reagent, the positioning information can be recorded, a specific area is selected from the image information and the reagent can be delivered automatically to the recorded specific area. For example, automation can be achieved using a mechanism that reads image information by a light microscope and records positioning information, a program that directs an ink-jet discharge to a specific area based on the recorded positioning information and a known ink-jet device that can be linked thereto or compose a system therewith. The mechanism that records the positioning information may be made capable of obtaining the positioning information of the target substance when an analysis is performed, and the localization of the target substance in the sample may be analyzed from the positioning information.

Unlike the conventional method, it is unnecessary to build physical compartments or the like on a sample because a very small amount of a reagent solution can be supplied to and retained in a very small area of a living sample as described above in the present invention. For this reason, working time may be reduced and sample damage caused by building compartments or the like can be avoided.

In the present invention, a molecule included in a specific tissue or cell in a living sample, preferably a molecule by which a specific tissue or a cell can be identified, or furthermore a specific molecule in a tissue or cell can be a target substance. For example, antigens (including a hapten), antibodies, enzymes and the like can be a target. And including these substances, in general, a protein, peptide, nucleic acid, sugar, lipid and the like can be a target substance. The reagents preferably used in the present invention are those that can detect the localization of a target substance in the living sample by making the target substance into a recognizable form (recognition) but are not restricted to these. If the localization of the target substance in a tissue or cell can be detected by these reagents, and the target substance is specific to the specific tissue or cell, the reagent can be an indicator to detect the localization of the tissue or the cell in the living sample. "Recognizable" as herein defined, means that which can be detected by visualization, mass spectrometry or the like.

In the present invention, a target substance can be made recognizable directly or indirectly using a substance that reacts with the target substance chemically or biologically (for example, a compound that reacts with the target substance or biorelated substance (hereinafter referred to as "living substance")) and a substance that specifically binds to the target substance (representative examples include antigen, antibody, nucleic acid and the like) as the reagent. As compounds which can chemically react with the target substance, compounds that can detect the target substance according to the chemical properties of the target substance by a normal method such as coloring, light emission, fluorescent emission and the like can be suitably used without particular restriction.

A substance binding specifically to the target substance may be a living substance or a synthetic substance. The living substance includes a protein, peptide, nucleic acid, sugar, lipid and the like and the specific binding property of these substances can be used. That is, the specific binding of an antigen to the corresponding antibody, an enzyme to the corresponding substrate, a nucleic acid to the corresponding nucleic acid can be used. Thus, a substance which binds specifically to the target substance can be used, for example, as an antibody, antigen and enzyme. An analogous compound such as an organic compound and metal complex that has the same or similar binding property to that of a living substance can be used as the synthetic compound described above. The analogous compound includes not only the one similar in structure but also the one that has the same or similar function of specific binding property as the living substance described above. Such an analogous compound includes a modified version of the living substance described above and an enzyme model. Also, depending on a method of recognition, the substance that specifically binds to these target substance may be the one to which a label is introduced. That is, the substance may be a labeled body labeled with a labeling substance or a complex body with the labeling substance.

When a living substance, which is the target substance in the living sample, is an antigen (including hapten) in the present invention, an immunohistochemical method can be used for recognition. The antigen includes a protein, peptide, nucleic acid, sugar, lipid and the like. The standard methods can be used as the immunohistochemical method. That is, a fluorescent antibody method, enzyme antibody method, heavy metal antibody method, radioisotope antibody method and the like can be used without particular restriction. Also, in these methods, any of labeled or non-labeled antibody method, or direct or indirect antibody method may be used. Therefore, the reagent of the present invention includes a protein and peptide, or protein and peptide to which a labeling substance is introduced, that is, a primary antibody and secondary antibody. Further, staining agents are included as the reagent when these antibodies are to be visualized by staining or the like.

The labeling substance can include a fluorescent substance, enzyme, heavy metal containing substance, radioisotope containing substance and other compounds. The fluorescent substance includes fluorescein isothiocyanate (FITC), tetramethyl rhodamine isothiocyanate (TRITC) and the like. The enzyme includes an endopeptidase, horseradish peroxidase, alkaline phosphatase, acid phosphatase, glucose oxidase, tyrosinase and the like. In particular, when a protein molecule degradation treatment method using endopeptidase was employed in combination with an ion-mass spectrometry such as MALDI or TOF-SIMS, the protein positioning information in the living sample can be obtained more efficiently. When analysis is performed by an ion-mass spectrometry such as the TOF-SIMS method, an intensifier can be added according to the method of the present invention. The intensifier refers to a substance that reacts to a peptide chain composing protein on the surface of the living sample and enhances the generation of the secondary ionic species. The intensifier includes, for example, a metal complex, homogeneous aqueous solution of metal chloride, aqueous solution of silver nitrate.

The heavy metal containing substance includes ferritin, gold colloid and the like. Other compound includes an enzyme model and the like. Further, biotin can be used as a labeling substance. Still further in this connection, a complex of labeled biotin and avidin, and labeled streptavidin can be used as the reagent.

The reagents shown above as examples may be used alone or as a mixture of two or more.

Further, the recognition of the target substance in the living sample is performed by the method corresponding to the antibody described above or the labeled substance introduced to the antibody. In particular, the recognition is performed by detecting color development, light emission, fluorescence, presence of a radioisotope, and the like. The target substance in the living sample made recognizable is analyzed by a microscopic observation or mass spectrometry.

When the microscopic observation is to be performed, for example, for an enzyme, the corresponding appropriate substrate solution is dispensed, then visualized by coloring or light emission method, and can be observed by a light microscope. For a fluorescent substance, it is visualized by a method of irradiating an appropriate excitation light to obtain fluorescence and can be observed by a fluorescence microscope or a laser microscope. For a substance containing a heavy metal, it is visualized by light scattering of irradiated light and can be observed by an electron microscope. For a radioisotope, it is visualized by the autoradiography method and can be observed.

When the living substance that is a target substance in the living sample is an enzyme in the present invention, the enzyme histochemistry method can be used for making the enzyme recognizable. In this case, the enzyme of the target substance can be made recognizable by the standard method using, as the aforementioned reagent, an appropriate substrate for the enzyme that is the target substance.

When the living substance that is the target substance in the living sample is a nucleic acid (including DNA and RNA) in the present invention, the in situ hybridization method can be used. In this case, the nucleic acid of the target substance can be made recognizable by the standard method using a labeled DNA probe as the reagent that can form a hybrid with the nucleic acid containing the target gene. The labeling substance for the labeled DNA includes the substances embodied in the immunohistochemistry method and may be determined appropriately by a person skilled in the art Mass spectrometry is performed, for example, by the time-of-flight secondary ion mass spectrometry (TOF-SIMS) or laser desorption ionization mass spectrometry (LDI-MS) methods. In the case of LDIMS method, the following operations are performed on the target substance that is made recognizable. First, the sample is subjected to digestion or the like as necessary. In digestion, for example, a protein digestive enzyme solution such as trypsin solution is added and incubated under a moist condition. Laser is irradiated on the target substance which has been treated as necessary to obtain a mass spectrum. Or a matrix solution is dispensed again as necessary to the aforementioned target substance, which has been treated as necessary, and laser is irradiated to the site of dispension to obtain a mass spectrum. Since in the present invention the dispensed area is limited to very small, unnecessary signals from the area other than the specified area, which are the background, can be reduced in the mass spectrum thus obtained. Furthermore, by performing the dispension of the matrix solution and the laser irradiation not only on one point on the sample but also in the predetermined range of the area repeatedly, an imaging based on mass distribution of the specific cell or tissue (detection of two dimensional conditions) can be obtained, and the mapping of the target substance on the living sample can be conducted. In the case of TOF-SIMS method, the methods for mass spectrum analysis and imaging can be performed using embodiments disclosed in Japanese Patent Application Laid-Open No. 2004-085546 and International Publication No. 2005/003715. The particular measuring conditions are as follows.

[Measuring Conditions for TOF-SIMS]
Equipment: TOF-SIMS IV made by ION TOF Inc.
<Primary Ion>
Primary ion: 25 kV, $Ga^+$, 0.6 pA (Pulse current value), random scan mode
Pulse frequency of primary ion: 2.5 kHz (400 μs/shot)
Pulse width of primary ion: 1 ns
Beam diameter of primary ion: 5 μm
<Secondary Ion>
Detection mode for secondary ion: positive
Measurement area: 300 μm×300 μm
Pixel number of secondary ion image: 128×128
Accumulation number: 256

According to these methods, the plurality of protein molecules, the detection targets, can be analyzed.

Further, analysis by mass spectrometry can be performed on the target substance that is not labeled. For example, when the reagent treatment of the present invention is a reaction that discriminates a specific tissue or cell by an indicator substance other than the target substance, then by performing mass spectrometry on the target substance after the reagent treatment, the target substance can be analyzed by correlating the target substance with the specific tissue or cell. For example, after reacting a labeled antibody, which detects a certain kind of cancer, to a sample according to the reagent treatment method of the present invention and detecting the label of the antibody to obtain the positioning information of the cancer tissue or cell, the cancer region and normal region can be compared by mass spectrometry, and the detected substance can be analyzed.

As described above, since the dispension of the reagent is limited to a very small compartment on the living sample according to the present invention, the consumed amount of the used reagent can be reduced greatly when compared to the conventional method. Furthermore, it is expected that many of the living samples are rare and difficult to obtain histopathological specimens. Since a plurality of analysis can be made on the same specimens, the living sample can be utilized more efficiently. Still further, on introducing mass spectrometry, a reduction of signals from the area other than where the reagent is dispensed, that is background, is expected.

EXAMPLES

Following is an example of analysis of the very fine area in a tissue section sample by TOF-SIMS method. For sample preparation, frozen sections of mouse brain are prepared and fixed on a silicon base.

Then, this section sample is stained by Direct Blue 71, and a thin-film containing a porous body (vertical pore, average pore diameter 3 μm, gap between pores 6 μm) made of a photoresist material is prepared by photolithography and is made close contact with the section sample of the living sample.

Figure 3A:
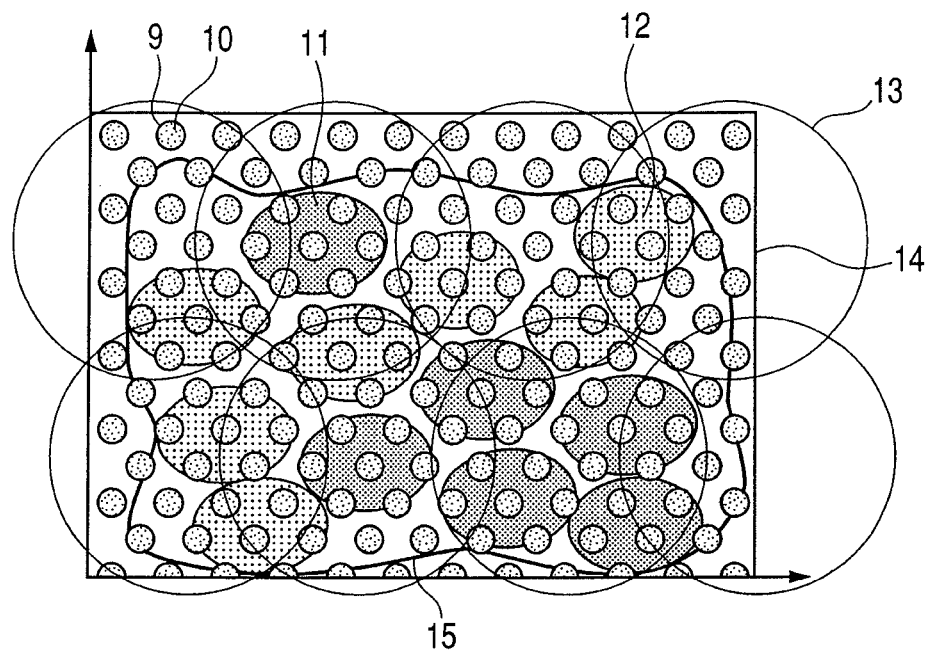
FIGS. 3A and 3B are views illustrating TOF-SIMS analysis of protein in a living sample degraded by trypsin of Examples.

After confirming the position of the pores of the porous body over the lesion cell that is the target of a light microscope, a phosphate buffer solution (pH 7.4) containing a dissolved digestive enzyme, trypsin, 10 μg/ml is placed in a ink-jet head reservoir and dispensed to the target location of pores in the area containing the lesion cells by 4 pl each by ink-jet (see FIG. 3A). At this time, the diameter of the area covered by a single drop of the digestive enzyme is about 30 μm, and the droplets are applied so that the covered areas are overlapped and the whole sample is covered. An appropriate amount of enzyme solution is continuously dispensed so that the solution is not lost due to drying, and after a predetermined time, water and low molecular mixed components in pores are evaporated off and the porous body thin-film is peeled off. By this procedure a living sample specimen can be obtained, on the surface of which digested and degradated peptide fragments are attached. The degradation products are detected by TOF-SIMS analysis. In this measurement, degradation products of various proteins and peptides are detected. For identification of a protein before degradation from the variety of ions of the degradation products produced by the limited digestion by a digestive enzyme, the disclosed results of the proteome analyses (various data base) can be utilized to find the peptide fragments derived from the specific protein or peptide.

Figure 3B:
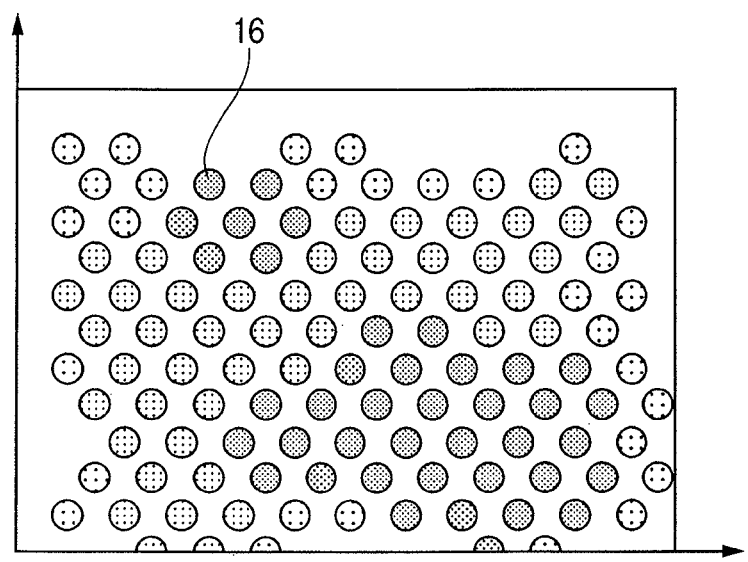

After TOF-SIMS analysis, imaging of the selected mass signal of the aforementioned fragment peptide resulted in the detection of the aforementioned signal at the specific location of the pore of the porous body as shown in FIG. 3B and thus the location of the object protein before the degradation can be determined. By using the method shown here, the distribution pattern of the components of the living sample can be grasped in each cell, and based on the distribution pattern in each cell, the sample, which is the measurement subject, can be determined whether it contains malignant or benign tumor. In addition, the presence or absence of a substance in the sample that is characteristic to a disease can be detected in each cell and thereby enabling an accurate diagnosis. Further, by contrasting the corresponding living sample's image measured by the microscopic observation and the two dimensional image display of the peak intensity of the secondary ion kinds, the localization of the object protein molecule on the surface of the living sample can be determined.

Further, the mass spectrometry and imaging methods in the present Examples can be performed using the embodiment disclosed in Japanese Patent Application Laid-Open No. 2004-085546. The particular measuring conditions that are suitably used are as follows.

[Measuring Conditions for TOF-SIMS]
Equipment: TOF-SIMS 5 made by ION TOF Inc.
<Primary Ion>
Primary ion: 25 kV, $Bi_3^+$, 0.25 pA
Pulse frequency of primary ion: 2.5 kHz (400 μs/shot)
Pulse width of primary ion: 2 ns
Beam diameter of primary ion: 5 μm
<Secondary Ion>
Detection mode for secondary ion: positive
Measurement area: 100×100 μm
Pixel number of secondary ion image: 128×128
Accumulation number: 256

According to a suitable embodiment of the present invention, a method for reagent treatment can be provided, in which a reagent can be supplied to an optional location on a living sample by limiting the area within the range of 10 μm, equivalent to a cell size, and a sufficient reactive production is performed by supplying and holding the reagent for a certain period of time while maintaining a specific structure in the area or a positioning information of component molecules thereof in each cell. In addition, an analytical method of the living sample using the reagent treatment method can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-277385, filed Oct. 11, 2006, which is hereby incorporated by reference herein in its entirety.

What is claimed is:

1. A method for providing a reagent to living cells in a sample comprising the steps of:
   providing a film having a thickness between 1 μm and 10 μm comprising a porous body and having a top face and opposite bottom face, wherein pores of the porous body are not interconnected to each other and are present independently, wherein the pores have a diameter of 10 nm to 10 μm, and are smaller than a diameter of the cells in the sample, and wherein the pores perforate through the film from the top face to the bottom face such that the pores are vertical or have an angle of 15° or less from the vertical;
   placing the living cells in the sample on a supporting member;
   contacting the bottom face of the film directly with the living cells on the supporting member such that each pore of the porous body corresponds to one living cell on the supporting member; and
   discharging by ink-jet a solution as a droplet containing at least one kind of reagent to the top face of the film not contacting the living cells such that the solution passes through the pores to the bottom face to contact the living cells to supply the reagent to each individual living cell separately.

2. The method for providing a reagent to living cells in a sample according to claim 1, wherein the reagent is a compound that reacts chemically or biologically with a target substance in one or more of the living cells.

3. The method for providing a reagent to living cells in a sample according to claim 1, further comprising a step of reading image information of the living cells to provide the reagent to each living cell of the sample by ink-jet in accordance with the image information.

4. A method for analyzing living cells in a sample, comprising the steps of:
   providing to living cells in the sample a reagent using the method according to claim 1; wherein the reagent reacts with a target substance in the living cells; and
   analyzing the living cells by microscopic observation or mass spectrometry, such that positioning information of the target substance is analyzed in each living cell.

5. The method for analyzing living cells in a sample according to claim 4, wherein the mass spectrometry is time-of-flight secondary ion mass spectrometry (TOF-SIMS).

* * * * *